United States Patent [19]

Denniston, Jr.

[11] 4,200,088
[45] Apr. 29, 1980

[54] REVERSIBLE VASECTOMY DEVICE AND METHOD

[75] Inventor: George C. Denniston, Jr., Seattle, Wash.

[73] Assignee: Ketchum Laboratories Inc., Amityville, N.Y.

[21] Appl. No.: 899,449

[22] Filed: Apr. 24, 1978

[51] Int. Cl.² ............................................. A61B 19/00
[52] U.S. Cl. .............................. 128/1 R; 128/303 R
[58] Field of Search ................... 128/1 R, 303 R, 341, 128/329; 339/100

[56] References Cited

U.S. PATENT DOCUMENTS

| | | | |
|---|---|---|---|
| 2,453,615 | 11/1948 | Bergan | 339/100 |
| 3,064,228 | 11/1962 | Knowlton | 339/100 |
| 3,589,355 | 6/1971 | Lee | 128/1 R |
| 3,613,661 | 10/1971 | Shah | 128/1 R |
| 3,648,683 | 3/1972 | Brodie | 128/1 R |
| 3,820,528 | 6/1974 | Rogers | 128/1 R |

*Primary Examiner*—Dalton L. Truluck
*Attorney, Agent, or Firm*—Blum, Kaplan, Friedman, Silberman & Beran

[57] ABSTRACT

A reversible vasectomy device and method which may be used to block the vas without the need for severing the vas. The invention includes a plug portion which may be inserted into a small hole in the vas to block it and an outer cylindrical portion which will surround the vas once inserted. The outer portion prevents the vas from dilating which would otherwise negate the effectiveness of the blockage.

12 Claims, 8 Drawing Figures

REVERSIBLE VASECTOMY DEVICE AND METHOD

BACKGROUND OF THE INVENTION

One of the major problems facing the world today is the crisis of potential overpopulation. One method of conrolling this crisis is the vasectomy operation. However, many men are discouraged from undergoing such an operation because of the fact that it is rarely reversible. A number of devices are known in the art for permitting reversible vasectomy operations. However, the methods and devices used are less than completely satisfactory because the vas may be damaged when it is severed.

The vas or vas deferens is a small 2.5 to 3 mm diameter tube running from the bottom of the testicles up to the scrotum and the inguinal canal behind the bladder where it joins the urethra. The function of the vas is to carry sperm from the testicle. The lower portion of the vas, near the testicle, is twisted upon itself but higher in the scrotum the vas straightens out and becomes somewhat larger (about 3 mm in diameter). It is this portion of the vas which is usually severed during a vasectomy and into which the device of the instant invention will be placed.

A cross-section of the vas reveals a small central lumen whose diameter is approximately one-tenth the total diameter of the vas. The lumen is stretchable and is surrounded by circular muscle fibers which in turn are surrounded by longitudinal muscle fibers and a very thin outer coating. The vas also contains numerous nerves. The purpose of the muscles and nerves is to squeeze the sperm up progressively along the lumen to the outside of the body. If the vas is cut the action of the vas is forever impaired even if it is reattached.

There have been a number of attempts in the past to block the vas without severing it. However, when objects have been inserted into the vas to block it, the lumen has simply dilated and the sperm traveled around the blockage. Furthermore, the vas often atrophies when blocked and this atrophy has also allowed the sperm to travel around the blockage. The present insertion provides a secure means for the blockage of the vas which will prevent dilation as well as avoidance of the blockage should the vas atrophy. The device and method also enhances reversability of the operation since the vas will not be severed during insertion and use.

SUMMARY OF THE INVENTION

Generally speaking, in accordance with the invention, a reversible vasectomy device and method is provided. The invention may be inserted into the vas by means of a simple hole in the vas without the need to sever the vas completely which may lead to problems in reversing the operation. The invention includes a plug portion which is inserted to block the vas and a cylindrical portion which will surround the outer portion of the vas to prevent it from dilating and thereby overcoming the blockage.

Accordingly, it is an object of this invention to provide an improved vasectomy device and method that is reversible.

Another object of this invention is to provide an improved vasectomy device and method that may be used to block the vas without the need for the vas to be severed.

A further object of the invention is to provide an improved vasectomy device and method which will not damage the vas.

Still another object of this invention is to provide an improved vasectomy device and method that will prevent negation of the operation by the dilation or atrophication of the vas.

Still other objects and advantages of the invention will in part be obvious and will in part be apparent from the specification.

The invention accordingly comprises the several steps and the relation of one or more of such steps with respect to each of the others, and the apparatus embodying features of construction, combinations of elements and arrangements of parts which are adapted to effect such steps, all as exemplified in the following detailed disclosure, and the scope of the invention will be indicated in the claims.

BRIEF DESCRIPTION OF THE DRAWINGS

For a fuller understanding of the invention, reference is had to the following description taken in connection with the accompanying drawings, in which.

DESCRIPTION OF THE PREFERRED EMBODIMENTS

Figure 1:
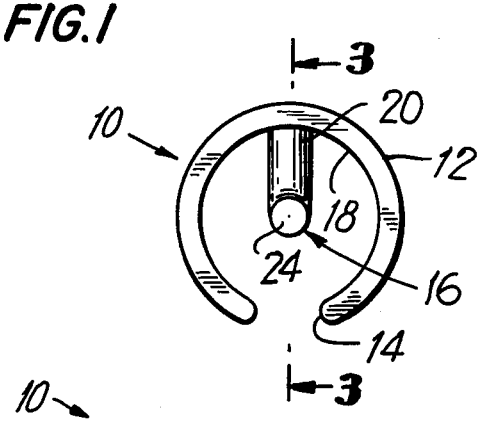
FIG. 1 is an end elevational view of a vasectomy device constructed in accordance with a preferred embodiment of the instant invention.
Figure 2:
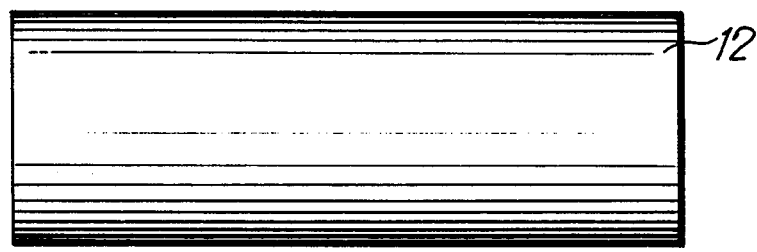
FIG. 2 is a side elevational view of the vasectomy device of the instant invention.
Figure 3:
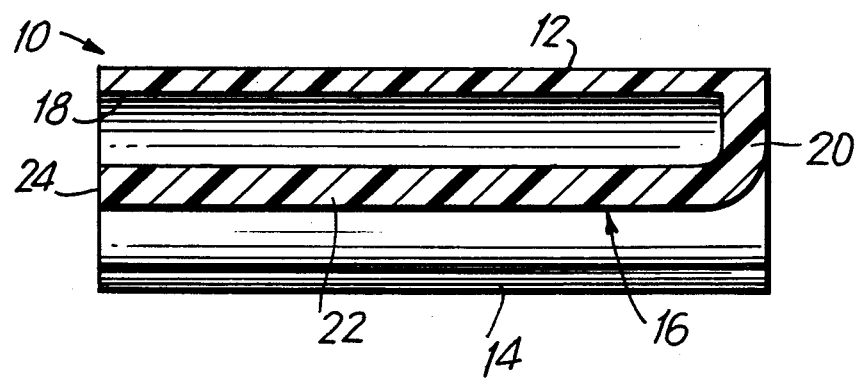
FIG. 3 is a sectional view taken along line 3—3 of FIG. 1.
Figure 3A:
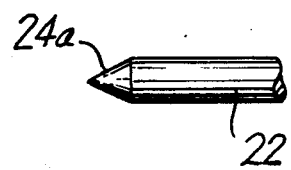
FIG. 3a shows another form of a preferred embodiment of the plug portion of the instant invention.
Figure 4:
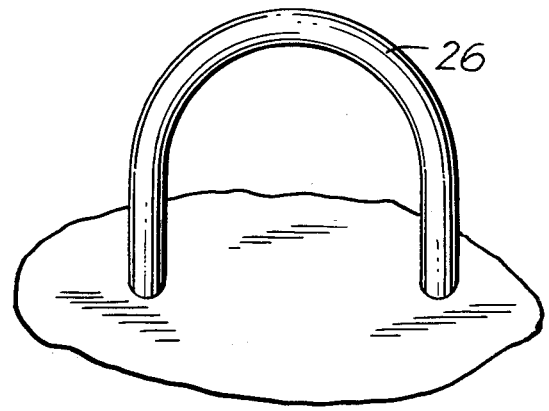
FIG. 4 is a persective view of the vas into which the device of the instant invention will be inserted.
Figure 5:
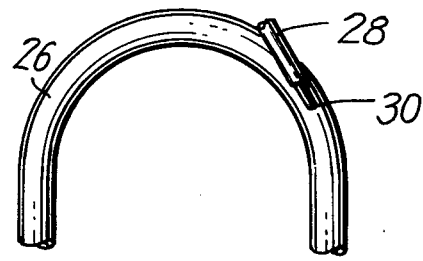
FIG. 5 is a view corresponding to that of FIG. 4 showing a needle puncturing the vas to prepare for insertion of the device.
Figure 6:
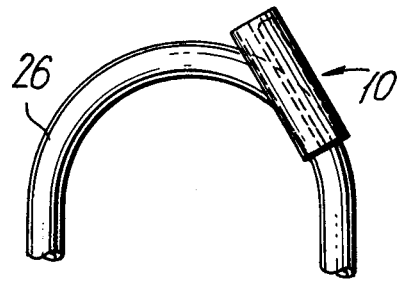
FIG. 6 is a perspective view of the device entering the vas.
Figure 7:
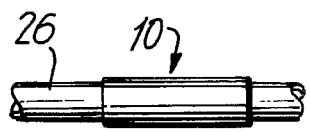
FIG. 7 shows the device of the instant invention in place on the vas.

The drawings illustrate a reversible vasectomy device generally indicated at 10. Device 10 consists of a elongated hollow cylindrical portion 12 which has a longitudinal slot 14 running along its entire length. Mounted within cylindrical portion 12 is a plug portion 16 which is mounted to the inner wall 18 of the cylindrical portion 12 at a portion 180° removed from slot 14. Plug portion 16 includes a radially extending section 20 fixed to one end of the cylindrical portion 12 and a longitudinal portion 22 running along the longitudinal axis of cylindrical portion 12 along its center line and along its entire length. The free end 24 of plug 16 may be square or pointed 24a as shown in FIG. 3a.

Suitable dimensions for device 10 are an overall length of 5 to 20 mm, an overall diameter of 2.5 to 3 mm with plug portion 16 being one-half to 1 mm in diameter. These dimensions are for illustrative purposes only and are not to be construed in any limiting sense. Of course, various other dimensions may be used in order to fit various vas in both humans and animals. The device may be injection molded as a unit from any suitable plastic, such as polypropylene. Additionally, a radio-opaque dye may also be added to the material forming the device 10 so that it may be seen when x-rays are taken. When inserted, plug proportion 16 will be inserted in the lumen of the vas to block sperm from traveling therethrough and cylindrical portion 12 will surround the outside of the vas. Cylindrical portion 12 is necessary because simply blocking the vas may result in its dilation and the sperm will travel around the blockage. The device also guards against the possibility of the vas atrophying (i.e. the walls becoming thinner).

FIGS. 4 through 7 illustrate the method of insertion of device 10 onto a loop of vas 26. The operation for insertion of device 10 may be performed under a local anesthetic. A one-half inch incision is made and vas 26 is brought out of the incision. The layers surrounding the vas are removed and a loop of vas 26 is obtained. A needle 28 is pushed into the lumen so that an opening 30 is made, device 10 is then grasped and the plug portion 16 is pushed through opening 30 made by needle 28. Cylindrical portion 12 is then slid over the outside of the vas in the direction towards the testicle. The vas is then straightened by allowing it to drop back into the scrotum and device 10 is firmly in place. If a device 10 is used including a pointed end 24a of plug portion 16, needle 28 need not be used since pointed end 24a will make its own opening 30.

The same procedure is repeated for the other side and a single suture closes the incision. A similarly simple operation is used to reverse the vasectomy. The device 10 may be felt through the skin and a small incision is again made after device 10 is located, it may be simply backed out of the vas and removed. The opening 30 in the vas in most cases will close up without difficulty. However, in certain cases, it may be necessary after removing device 10 to seal the hole with some surgical sealant in order to prevent sperm leakage.

It will thus be seen that the objects set forth above, among those made apparent from the preceding description, are efficiently attained and, since certain changes may be made in carrying out the above method and in the article set forth without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed is:

1. A vasectomy device for blocking the vas deferens and lumen comprising an elongated housing for surrounding and abutting at least a portion of the periphery of said vas deferens to prevent dilation thereof said housing having slot means extending therealong to permit positioning of the housing on the vas, said housing being provided with plug means attached thereto and extending axially along the interior of said housing for blocking sperm flow through said lumen.

2. A vasectomy device as claimed in claim 1 wherein said plug means includes a circular cross-section.

3. The vasectomy device as claimed in claim 1 wherein said plug means and said housing are of one-piece construction.

4. The vasectomy device as claimed in claim 1 wherein said housing is cylindrical.

5. A vasectomy device as claimed in claim 4 wherein said cylindrical housing includes a longitudinal slot.

6. A vasectomy device as claimed in claim 1 wherein said plug means comprise a cylindrical member.

7. A vasectomy device as claimed in claim 6 wherein said plug means has a pointed end which may be used to puncture the vas deferns for insertion of said device.

8. A vasectomy device as claimed in claim 1 wherein said device is manufactured from polypropylene.

9. A vasectomy device as claimed in claim 1 wherein said device contains a radio-opaque material for rendering said device visible during x-rays.

10. A vasectomy device as claimed in claim 1 wherein said housing is a cylinder 5 to 20 mm in length and 2.5 to 3 mm in diameter.

11. A vasectomy device as claimed in claim 1 wherein said plug means comprising a cylindrical member ½ into 1 mm in diameter.

12. A vasectomy device as claimed in claim 1 wherein said housing comprises a hollow cylinder having a longitudinal slot running the entire length thereof, said plug means comprising a cylindrical member extending along the center line of said cylindrical housing and being joined thereto at one end thereof.

* * * * *